(12) United States Patent
Thompson et al.

(10) Patent No.: US 7,601,806 B2
(45) Date of Patent: Oct. 13, 2009

(54) RTVP-GLIPR-LIKE COMPOSITIONS AND METHODS FOR THE DETECTION, TREATMENT AND PREVENTION OF PROSTATE CANCER

(75) Inventors: Timothy C. Thompson, Houston, TX (US); Chenghui Ren, Houston, TX (US); Chengzhen Ren, Pearland, TX (US)

(73) Assignee: Baylor College of Medicine, Houston, TX (US)

(*) Notice: Subject to any disclaimer, the term of this patent is extended or adjusted under 35 U.S.C. 154(b) by 216 days.

(21) Appl. No.: 10/559,994

(22) PCT Filed: Jun. 8, 2004

(86) PCT No.: PCT/US2004/018731

§ 371 (c)(1),
(2), (4) Date: Apr. 28, 2006

(87) PCT Pub. No.: WO2004/111200

PCT Pub. Date: Dec. 23, 2004

(65) Prior Publication Data

US 2006/0240025 A1    Oct. 26, 2006

(51) Int. Cl.
*C07K 14/00* (2006.01)

(52) U.S. Cl. .................................................... 530/350
(58) Field of Classification Search ...................... None
See application file for complete search history.

(56) References Cited

U.S. PATENT DOCUMENTS 5,912,143 A * 6/1999 Bandman et al. ........... 435/69.1

FOREIGN PATENT DOCUMENTS

WO    WO 00/59938    * 10/2000

OTHER PUBLICATIONS

Ezell (J. NIH Res, 1995, 7:46- 49 ).*
Spitler (Cancer Biotherapy, 1995, 10:1- 3)*
Boon (Adv Can Res, 1992, 58:177-210).*
DeGruijl et al (Nature Medicine, 5410): 1124-1125, Oct. 1999).*
Rich, et al., "RTVP-1, a novel human gene with sequence similarity to genes of diverse species is expressed in tumor cell lines of glial but not neuronal origin," *Gene* 180:125-130 (1996).
International Search Report dated Jul. 28, 2005.

* cited by examiner

*Primary Examiner*—Christopher H Yaen
(74) *Attorney, Agent, or Firm*—Vinson & Elkins L.L.P.

(57) ABSTRACT

The invention is directed to purified and isolated novel RGL polypeptides, the nucleic acids encoding such polypeptides, processes for production of recombinant forms of such polypeptides, antibodies generated against these polypeptides, fragmented peptides derived from these polypeptides, and the uses of the above.

8 Claims, 8 Drawing Sheets

FIGURE 1

RTVP and RGL1α, RGL1β DNA compare

```
RTVP-1       1 CTCTGTTTTCTCAAAGCTGAAGTCGGCTAGGTTTGCAAAGCTGTGGGCTG
RGLα         1 --------------------------------------------------
RGLβ         1 --------------------------------------------------
consensus    1

RTVP-1      51 AGCACTCAGGCAATCACACTCTCAGAAACTGCGGCGGCTCTGGACTGCAG
RGLα         1 ------------------------CATCCTCCGCATC-CTCCAC---AT
RGLβ         1 ------------------------CATCCTCCGCATC-CTCCAC---AT
consensus   51                         cAtCctCcGCatC CTccAC    At RTVP-1     101 CCTCCCAAGGCTCCATGCCAGACAAAGCATGCGTGTCACACTTGCTACAA
RGLα        22 CCTTCCATGGCTC--TG-------AAGAATAAATT---CAGTTGTTTATG
RGLβ        22 CCTTCCATGGCTC--TG-------AAGAATAAATT---CAGTTGTTTATG
consensus  101 CCTtCCAtGGCTC  TG       AAGaATaaaTt   CAgTTGtTtatg RTVP-1     151 TAGCCTGGATGGTTTCTTTTGTCTCCAATTATTCACACACAGCAAATATT
RGLα        60 GATCTTGGGTC-TGTGTTTGGTAGCCACTACATCTTCCA----AAATC--
RGLβ        60 GATCTTGGGTC-TGTGTTTGGTAGCCACTACATCTTCCA----AAATC--
consensus  151 gAtCtTGGgTc TgTgTTTgGTagCCAcTacaTCttcCA    AAATc RTVP-1     201 TTGCCAGATATCGAAAATGAAGATTTCATCAAAGACTGCGTTCGAATCCA
RGLα       103 ---CCATCCATCACTGACCCACACTTTATAGACAACTGCATAGAAGCCCA
RGLβ       103 ---CCATCCATCACTGACCCACACTTTATAGACAACTGCATAGAAGCCCA
consensus  201    CCAtccATCactgAcccAcAcTTtATagAcaACTGCaTagaAgcCCA RTVP-1     251 TAACAAGTTCCGATCAGAGGTGAAACCAACAGCCAGTGATATGCTATACA
RGLα       150 CAACGAATGGCGTGGCAAAGTCAACCCTCCCGCGGCCGACATGAAATACA
RGLβ       150 CAACGAATGGCGTGGCAAAGTCAACCCTCCCGCGGCCGACATGAAATACA
consensus  251 cAACgAaTggCGtggcaAaGTcAAcCCTcCcGCggccGACATGaaATACA RTVP-1     301 TGACTTGGGACCCAGCACTAGCCCAAATTGCAAAAGCATGGGCCAGCAAT
RGLα       200 TGATTTGGGATAAAGGTTTAGCAAAGATGGCTAAAGCATGGGCAAACCAG
RGLβ       200 TGATTTGGGATAAAGGTTTAGCAAAGATGGCTAAAGCATGGGCAAACCAG
consensus  301 TGAtTTGGGAtaaAGgttTAGCaaAgATgGCtAAAGCATGGGCaAaCcAg RTVP-1     351 TGCCAGTTTTCACATAATACACGGCTGAAGCCACCCCACAAGCTGC-ACC
RGLα       250 TGCAAATTTGAACATAATGACTGTTTGGATAAATCATATAAA-TGCTATG
RGLβ       250 TGCAAATTTGAACATAATGACTGTTTGGATAAATCATATAAA-TGCTATG
consensus  351 TGCaAaTTTgaACATAATgactGttTGgAtaaAtCatAtAAa TGCtAtg RTVP-1     400 CAAACTTCACTTCACTGGGAGAGAACATCTGGACTGG--GTCTGTGCCCA
RGLα       299 CAGCTTTTGAATATGTTGGAGAAAATATCTGGTTAGGTGGAATAAAGTCA
RGLβ       299 CAGCTTTTGAATATGTTGGAGAAAATATCTGGTTAGGTGGAATAAAGTCA
```

FIGURE 1 CONTINUED

```
consensus  401  CAgctTTtgaaTatgTtGGAGAaAAtATCTGGttaGGtgGaaTaaagtCA

RTVP-1     448  TTTTTTCTGTGTCTTCCGCCATCACAAACTGGTATGACGAAATCCAGGAC
RGLα       349  TTCACACCAAGACAT--GCCATTACGGCTTGGTATAATGAAACCCAATTT
RGLβ       349  TTCACACCAAGACAT--GCCATTACGGCTTGGTATAATGAAACCCAATTT
consensus  451  TTcacaCcaaGaCaT  GCCATtACggctTGGTATAatGAAAcCCAattt RTVP-1     498  TATGACTTCAAGACTCGGATATGCAAAAAAGTCTGTGGCCACTACACTCA
RGLα       397  TATGATTTTGATAGTCTATCATGCTCCAGAGTCTGTGGCCATTATACACA
RGLβ       397  TATGATTTTGATAGTCTATCATGCTCCAGAGTCTGTGGCCATTATACACA
consensus  501  TATGAtTTtgAtAgTCtatcATGCTccAgAGTCTGTGGCCAttAtACaCA RTVP-1     548  GGTTGTTTGGGCAGATAGTTACAAAGTTGGCTGCGCAGTTCAATTTTGCC
RGLα       447  GTTAGTTTGGGCCAATTCATTTTATGTCGGTTGTGCAGTTGCAATGTGTC
RGLβ       447  GTTAGTTTGGGCCAATTCATTTTATGTCGGTTGTGCAGTTGCAATGTGTC
consensus  551  GtTaGTTTGGGCcaATTcaTtttAtGTcGGtTGtGCAGTTgcAaTgTGtC RTVP-1     598  CTAAAGTTTCTGGCTTTGACGCTCTTTCCAATGGAGCACATTTTATATGC
RGLα       497  CTAA---------CCTTGGGGGAGCTTCAACTGCAATA---TTTGTATGC
RGLβ       497  CTAA---------CCTTGGGGGAGCTTCAACTGCAATA---TTTGTATGC
consensus  601  CTAA         CcTTGggGgagCTTCaAcTGCAatA   TTTgTATGC RTVP-1     648  AACTACGGACCAGGAGGGAATTACCCAACTTGGCCATATAA---GAGAGG
RGLα       535  AACTACGGACCTGCAGGAAATTTTGCAAATATGCCTCCTTACGTAAGAGG
RGLβ       535  AACTACGGACCTGCAGGAAATTTTGCAAATATGCCTCCTTACGTAAGAGG
consensus  651  AACTACGGACCtGcAGGaAATTttgCAAaTatGCCtccTTAcgtaAGAGG RTVP-1     695  AGCCACCTGCAGTGCCTGCCCCAATAATGACAAGTGTTTGGACAATCTCT
RGLα       585  AGAATCTTGCTCTCTCTGCTCAAAAGAAGAGAAATGTGTAAAGAACCTCT
RGLβ       585  AGAATCTTGCTCTCTCTGCTCAAAAGAAGAGAAATGTGTAAAGAACCTCT
consensus  701  AGaatCtTGCtcTctCTGCtCaAAagAaGAgAAaTGTgTaaAgAAcCTCT RTVP-1     745  GTGTTAACCGACAGCGAGACCAAGTGAAACGTTACTACTCTGTTGTATAT
RGLα       635  GCA-------------------------------AAAATCCATTTCTGAAG
RGLβ       635  GCAGGACTCCACAACTTATTATACCTAACC---AAAATCCATTTCTGAAG
consensus  751  Gca   a   c  acagc   g     a     aa c    AaaAtcCatTTcTgaAg RTVP-1     795  CCAGGCTGGCCCATATATCCACGTAACAGATACACTTCTCTCTTTCTCAT
RGLα       655  CCAACGGGG-----AGAGCACCTCAGCAGACAGCCTTTAATCCAT-TCAG
RGLβ       682  CCAACGGGG-----AGAGCACCTCAGCAGACAGCCTTTAATCCAT-TCAG
consensus  801  CCAacggGG     AgAgCacCtcAgCAGAcAgcCTTTaaTCcaT TCAg RTVP-1     845  TGTTAATTCAGTAATTCTAATACTGTCTGTTATAATTACCATTTTGGTAC
RGLα       699  CTTAGGTTTTCTTCTTCTGAGAAT--CTTTTAATGT---CATTTATATAC
RGLβ       726  CTTAGGTTTTCTTCTTCTGAGAAT--CTTTTAATGT---CATTTATATAC
consensus  851  ctTaggTTttcTtcTTCTgAgAaT  CTtTTAatgT   CATTTataTAC RTVP-1     895  AGCTCAAGTACCCTAATTTAGTTCTTTTGGACTAATACAATTCAGGAA-A
RGLα       744  AAAAGAAATTCTCAAATGT---------------TAAAATAAAGGAATA
```

FIGURE 1 CONTINUED

```
RGLβ        771  AAAAGAAATTCTCAAATGT---------------TAAAATAAAGGAATA
consensus   901  AaaagAAaTtCtCaAATgT               TAaAATaaAGGAAtA RTVP-1      944  GAAAAAACCCAAAAACCAACCTCATTCACATATGGCTTTTTT--TTAACC
RGLα        778  GTTTATTGCTTAATATAA--CTTATCATCACTTTGCTTCTTTACTGAATC
RGLβ        805  GTTTATTGCTTAATATAA--CTTATCATCACTTTGCTTCTTTACTGAATC
consensus   951  GtttAttgCttAatAtaA  CTtATcatCActTtGCTTcTTTacTgAAtC

RTVP-1      992  AATAACAATTAGGTGTACTTCTATTTTAAAACATTTCAGAAAAAAATA

RGLα        826  TTCTACACTCTTGC---CTGATACCTAAA------(SEQ ID NO: 1)

RGLβ        853  TTCTACACTCTTGC---CTGATACCTAA-------(SEQ ID NO: 3)

consensus  1001  ttctACAcTcttGc    CTgaTAccTaAA
```

FIGURE 2

RTVP-1 and RGL1α, RGL1β protein compare

```
RTVP-1      MRVTLATIAWMVSFVSNYSHTANILPDIENEDFIKDCVRIHNKFRSEVKPTASDMLYMTW
            ...,  .. . :..  .:.:..  .::..:.  ::..:..:.:.:.:: ::.:
RGLα        MALKNKFSCLWILGLCLVATTSSKIPSITDPHFIDNCIEAHNEWRGKVNPPAADMKYMIW
            ::::::::::::::::::::::::::::::::::::::::::::::::::::::::::
RGLβ        MALKNKFSCLWILGLCLVATTSSKIPSITDPHFIDNCIEAHNEWRGKVNPPAADMKYMIW
            1                                                          60

RTVP-1      DPALAQIAKAWASNCQFSHNTRLKPPHKLHPNFTSLGENIWTGSVPIFSVSSAITNWYDE
            :  .::..:::::..:.:.::.  :.  ...:  ....:.  .:::::  :...  :. . :::.::.:
RGLα        DKGLAKMAKAWANQCKFEHNDCLDKSYKCYAAFEYVGENIWLGGIKSFTPRHAITAWYNE
            ::::::::::::::::::::::::::::::::::::::::::::::::::::::::::
RGLβ        DKGLAKMAKAWANQCKFEHNDCLDKSYKCYAAFEYVGENIWLGGIKSFTPRHAITAWYNE

RTVP-1      IQDYDFKTRICKKVCGHYTQVVWADSYKVGCAVQFCPKVSGFDALSNGAHFICNYGPGGN
            .:  :::..   :...::::::.::::.  ::::::..::,..:          ...:  :.:::::.::
RGLα        TQFYDFDSLSCSRVCGHYTQLVWANSFYVGCAVAMCPNLGG----ASTAIFVCNYGPAGN
            ::::::::::::::::::::::::::::::::::::::::::::::::::::::::::
RGLβ        TQFYDFDSLSCSRVCGHYTQLVWANSFYVGCAVAMCPNLGG----ASTAIFVCNYGPAGN

RTVP-1      YPTW-PYKRGATCSACPNNDKCLDNLC---------------VNRQRDQVK-RYYSVVY
            ... ::  ::...:^ :V...::..:::          .:....:.   ..:.  .
RGLα        FANMPPYVRGESCSLCSKEEKCVKNLCK---------NPFLKPTGRAPQQTAFNPFSLGF
            :::::::::::::::::::::::::::.          ::::::::::::::::::::
RGLβ        FANMPPYVRGESCSLCSKEEKCVKNLCRTPQLIIPNQNPFLKPTGRAPQQTAFNPFSLGF

RTVP        PGWPIYPRNRYTSLFLIVNSVILILSVIITILVQLKYPNLVLLD
            .:
RGLα        LLLRIF      (SEQ ID NO: 2)
            ::::::
RGLβ        LLLRIF      (SEQ ID NO: 4)
``` signal peptide           MQVILAVIVWM
    SCP-domain(sig1,sig2)    VCGHYTQVVWAD
    Caveolin biding site     YNETQFYDF
    TM-domain                YTSLFLIVNSVILILSVIITILV

FIGURE 3

RGL1 p53 binding sites
( Promoter 4kb--intron 4 )

Intron 1
- 581 AAATAAGTTC AAAACT GTACTAGTCT 90% (A)
- Intron 2
- 1359 AGACTAGTTT CTTCAC ATACATGTTT 95% (B)
- 1557 AAGCCTGTTT AAGCAATATAAA GAGCTAACCT
  TCTTCTCT AGACTTACCC 90% (C1, C2)
- 16403     GAGCTTACTC TTTAT TGGCTAGTTT 90% (D)
- Intron 3
- 3116 AGATAAGTCT GA GGTCTTGTCT 90% (E)
- 32226     AGACAAGCCA CCTGG AAGAAAGTCT 90% (F)
- Intron 4
- 35786     AAACAAACTT T AGACAAGTTT 95% (G)
- 36649     TAACTAGTTT GGGTACTAGTAAACC
  TGGCATGCCC TC AAACTTTTTC 90% (H1, H2)
- 38942     AGACATTCTC TATA AAGCTATTTT 90% (I)

SEQUENCE LISTING

<160> NUMBER OF SEQ ID NOS: 4

<210> SEQ ID NO 1
<211> LENGTH: 851
<212> TYPE: DNA
<213> ORGANISM: Homosapiens
<220> FEATURE:
<221> NAME/KEY: CDS
<222> LOCATION: (28)..(726)

<400> SEQUENCE: 1

```
catcctccgc atcctccaca tccttcc atg gct ctg aag aat aaa ttc agt tgt        54
                                Met Ala Leu Lys Asn Lys Phe Ser Cys
                                 1               5 tta tgg atc ttg ggt ctg tgt ttg gta gcc act aca tct tcc aaa atc         102
Leu Trp Ile Leu Gly Leu Cys Leu Val Ala Thr Thr Ser Ser Lys Ile
 10              15                  20                  25 cca tcc atc act gac cca cac ttt ata gac aac tgc ata gaa gcc cac         150
Pro Ser Ile Thr Asp Pro His Phe Ile Asp Asn Cys Ile Glu Ala His
                 30                  35                  40 aac gaa tgg cgt ggc aaa gtc aac cct ccc gcg gcc gac atg aaa tac         198
Asn Glu Trp Arg Gly Lys Val Asn Pro Pro Ala Ala Asp Met Lys Tyr
             45                  50                  55 atg att tgg gat aaa ggt tta gca aag atg gct aaa gca tgg gca aac         246
Met Ile Trp Asp Lys Gly Leu Ala Lys Met Ala Lys Ala Trp Ala Asn
         60                  65                  70 cag tgc aaa ttt gaa cat aat gac tgt ttg gat aaa tca tat aaa tgc         294
Gln Cys Lys Phe Glu His Asn Asp Cys Leu Asp Lys Ser Tyr Lys Cys
     75                  80                  85 tat gca gct ttt gaa tat gtt gga gaa aat atc tgg tta ggt gga ata         342
Tyr Ala Ala Phe Glu Tyr Val Gly Glu Asn Ile Trp Leu Gly Gly Ile
 90                  95                 100                 105 aag tca ttc aca cca aga cat gcc att acg gct tgg tat aat gaa acc         390
Lys Ser Phe Thr Pro Arg His Ala Ile Thr Ala Trp Tyr Asn Glu Thr
                110                 115                 120 caa ttt tat gat ttt gat agt cta tca tgc tcc aga gtc tgt ggc cat         438
Gln Phe Tyr Asp Phe Asp Ser Leu Ser Cys Ser Arg Val Cys Gly His
            125                 130                 135 tat aca cag tta gtt tgg gcc aat tca ttt tat gcc ggt tgt gca gtt         486
Tyr Thr Gln Leu Val Trp Ala Asn Ser Phe Tyr Ala Gly Cys Ala Val
        140                 145                 150 gca atg tgt cct aac ctt ggg gga gct tca act gca ata ttt gta tgc         534
Ala Met Cys Pro Asn Leu Gly Gly Ala Ser Thr Ala Ile Phe Val Cys
    155                 160                 165 aac tac gga cct gca gga aat ttt gca aat atg cct cct tac gta aga         582
Asn Tyr Gly Pro Ala Gly Asn Phe Ala Asn Met Pro Pro Tyr Val Arg
170                 175                 180                 185 gga gaa tct tgc tct ctc tgc cca aaa gaa gag aaa tgt gta aag aac         630
Gly Glu Ser Cys Ser Leu Cys Pro Lys Glu Glu Lys Cys Val Lys Asn
                190                 195                 200 ctc tgc aaa aat cca ttt ctg aag cca acg ggg aga gca cct cag cag         678
Leu Cys Lys Asn Pro Phe Leu Lys Pro Thr Gly Arg Ala Pro Gln Gln
            205                 210                 215 aca gcc ttt aat cca ttc agc tta ggt ttt ctt ctg aga atc ttt             726
Thr Ala Phe Asn Pro Phe Ser Leu Gly Phe Leu Leu Arg Ile Phe
        220                 225                 230
```

```
taatgtcatt tatatacaaa agaaattctc aaatgttaaa ataaaggaat agtttattgc      786
ttaatataac ttatcatcac tttgcttctt tactgaatct tctacactct tgcctgatac      846
ctaaa                                                                  851
```

```
<210> SEQ ID NO 2
<211> LENGTH: 233
<212> TYPE: PRT
<213> ORGANISM: Homosapiens

<400> SEQUENCE: 2
```

```
Met Ala Leu Lys Asn Lys Phe Ser Cys Leu Trp Ile Leu Gly Leu Cys
1               5                   10                  15

Leu Val Ala Thr Thr Ser Ser Lys Ile Pro Ser Ile Thr Asp Pro His
            20                  25                  30

Phe Ile Asp Asn Cys Ile Glu Ala His Asn Glu Trp Arg Gly Lys Val
        35                  40                  45

Asn Pro Pro Ala Ala Asp Met Lys Tyr Met Ile Trp Asp Lys Gly Leu
    50                  55                  60

Ala Lys Met Ala Lys Ala Trp Ala Asn Gln Cys Lys Phe Glu His Asn
65                  70                  75                  80

Asp Cys Leu Asp Lys Ser Tyr Lys Cys Tyr Ala Ala Phe Glu Tyr Val
                85                  90                  95

Gly Glu Asn Ile Trp Leu Gly Ile Lys Ser Phe Thr Pro Arg His
            100                 105                 110

Ala Ile Thr Ala Trp Tyr Asn Glu Thr Gln Phe Tyr Asp Phe Asp Ser
        115                 120                 125

Leu Ser Cys Ser Arg Val Cys Gly His Tyr Thr Gln Leu Val Trp Ala
    130                 135                 140

Asn Ser Phe Tyr Ala Gly Cys Ala Val Ala Met Cys Pro Asn Leu Gly
145                 150                 155                 160

Gly Ala Ser Thr Ala Ile Phe Val Cys Asn Tyr Gly Pro Ala Gly Asn
                165                 170                 175

Phe Ala Asn Met Pro Pro Tyr Val Arg Gly Glu Ser Cys Ser Leu Cys
            180                 185                 190

Pro Lys Glu Glu Lys Cys Val Lys Asn Leu Cys Lys Asn Pro Phe Leu
        195                 200                 205

Lys Pro Thr Gly Arg Ala Pro Gln Gln Thr Ala Phe Asn Pro Phe Ser
    210                 215                 220

Leu Gly Phe Leu Leu Leu Arg Ile Phe
225                 230
```

```
<210> SEQ ID NO 3
<211> LENGTH: 877
<212> TYPE: DNA
<213> ORGANISM: Homosapiens
<220> FEATURE:
<221> NAME/KEY: CDS
<222> LOCATION: (28)..(753)

<400> SEQUENCE: 3
catcctccgc atcctccaca tccttcc atg gct ctg aag aat aaa ttc agt tgt     54
                                Met Ala Leu Lys Asn Lys Phe Ser Cys
                                1               5 tta tgg atc ttg ggt ctg tgt ttg gta gcc act aca tct tcc aaa atc     102
Leu Trp Ile Leu Gly Leu Cys Leu Val Ala Thr Thr Ser Ser Lys Ile
    10                  15                  20                  25
```

```
cca tcc atc act gac cca cac ttt ata gac aac tgc ata gaa gcc cac      150
Pro Ser Ile Thr Asp Pro His Phe Ile Asp Asn Cys Ile Glu Ala His
             30                  35                  40 aac gaa tgg cgt ggc aaa gtc aac cct ccc gcg gcc gac atg aaa tac      198
Asn Glu Trp Arg Gly Lys Val Asn Pro Pro Ala Ala Asp Met Lys Tyr
         45                  50                  55 atg att tgg gat aaa ggt tta gca cag atg gct aaa gca tgg gca aac      246
Met Ile Trp Asp Lys Gly Leu Ala Gln Met Ala Lys Ala Trp Ala Asn
     60                  65                  70 cag tgc aaa ttt gaa cat aat gac tgt ttg gat aaa tca tat aaa tgc      294
Gln Cys Lys Phe Glu His Asn Asp Cys Leu Asp Lys Ser Tyr Lys Cys
 75                  80                  85 tat gca gct ttt gaa tat gtt gga gaa aat atc tgg tta ggt gga ata      342
Tyr Ala Ala Phe Glu Tyr Val Gly Glu Asn Ile Trp Leu Gly Gly Ile
 90                  95                 100                 105 aag tca ttc aca cca aga cat gcc att acg gct tgg tat aat gaa acc      390
Lys Ser Phe Thr Pro Arg His Ala Ile Thr Ala Trp Tyr Asn Glu Thr
                110                 115                 120 caa ttt tat gat ttt gat agt cta tca tgc tcc aga gtc tgt ggc cat      438
Gln Phe Tyr Asp Phe Asp Ser Leu Ser Cys Ser Arg Val Cys Gly His
            125                 130                 135 tat aca cag tta gtt tgg gcc aat tca ttt tat gtc ggt tgt gca gtt      486
Tyr Thr Gln Leu Val Trp Ala Asn Ser Phe Tyr Val Gly Cys Ala Val
        140                 145                 150 gca atg tgt cct aac ctt ggg gga gct tca act gca ata ttt gta tgc      534
Ala Met Cys Pro Asn Leu Gly Gly Ala Ser Thr Ala Ile Phe Val Cys
    155                 160                 165 aac tac gga cct gca gga aat ttt gca aat atg cct cct tac gta aga      582
Asn Tyr Gly Pro Ala Gly Asn Phe Ala Asn Met Pro Pro Tyr Val Arg
170                 175                 180                 185 gga gaa tct tgc tct ctc tgc tca aaa gaa gag aaa tgt gta aag aac      630
Gly Glu Ser Cys Ser Leu Cys Ser Lys Glu Glu Lys Cys Val Lys Asn
                190                 195                 200 ctc tgc agg act cca caa ctt att ata cct aac caa aat cca ttt ctg      678
Leu Cys Arg Thr Pro Gln Leu Ile Ile Pro Asn Gln Asn Pro Phe Leu
            205                 210                 215 aag cca acg ggg aga gca cct cag cag aca gcc ttt aat cca ttc agc      726
Lys Pro Thr Gly Arg Ala Pro Gln Gln Thr Ala Phe Asn Pro Phe Ser
        220                 225                 230 tta ggt ttt ctt ctt ctg aga atc ttt taatgtcatt tatatacaaa            773
Leu Gly Phe Leu Leu Leu Arg Ile Phe
    235                 240 agaaattctc aaatgttaaa ataaggaat agtttattgc ttaatataac ttatcatcac     833
tttgcttctt tactgaatct tctacactct tgcctgatac ctaa                     877

<210> SEQ ID NO 4
<211> LENGTH: 242
<212> TYPE: PRT
<213> ORGANISM: Homosapiens

<400> SEQUENCE: 4

Met Ala Leu Lys Asn Lys Phe Ser Cys Leu Trp Ile Leu Gly Leu Cys
1               5                   10                  15

Leu Val Ala Thr Thr Ser Ser Lys Ile Pro Ser Ile Thr Asp Pro His
            20                  25                  30

Phe Ile Asp Asn Cys Ile Glu Ala His Asn Glu Trp Arg Gly Lys Val
        35                  40                  45

Asn Pro Pro Ala Ala Asp Met Lys Tyr Met Ile Trp Asp Lys Gly Leu
    50                  55                  60
```

-continued

```
Ala Gln Met Ala Lys Ala Trp Ala Asn Gln Cys Lys Phe Glu His Asn
 65              70                  75              80

Asp Cys Leu Asp Lys Ser Tyr Lys Cys Tyr Ala Ala Phe Glu Tyr Val
             85              90                  95

Gly Glu Asn Ile Trp Leu Gly Gly Ile Lys Ser Phe Thr Pro Arg His
            100             105             110

Ala Ile Thr Ala Trp Tyr Asn Glu Thr Gln Phe Tyr Asp Phe Asp Ser
            115             120             125

Leu Ser Cys Ser Arg Val Cys Gly His Tyr Thr Gln Leu Val Trp Ala
        130             135             140

Asn Ser Phe Tyr Val Gly Cys Ala Val Ala Met Cys Pro Asn Leu Gly
145             150             155             160

Gly Ala Ser Thr Ala Ile Phe Val Cys Asn Tyr Gly Pro Ala Gly Asn
            165             170             175

Phe Ala Asn Met Pro Pro Tyr Val Arg Gly Glu Ser Cys Ser Leu Cys
            180             185             190

Ser Lys Glu Glu Lys Cys Val Lys Asn Leu Cys Arg Thr Pro Gln Leu
        195             200             205

Ile Ile Pro Asn Gln Asn Pro Phe Leu Lys Pro Thr Gly Arg Ala Pro
        210             215             220

Gln Gln Thr Ala Phe Asn Pro Phe Ser Leu Gly Phe Leu Leu Leu Arg
225             230             235             240

Ile Phe
```

RTVP-GLIPR-LIKE COMPOSITIONS AND METHODS FOR THE DETECTION, TREATMENT AND PREVENTION OF PROSTATE CANCER

RIGHTS IN THE INVENTION

The invention was made with support from the United States government under grant numbers RO1-CA50588, RO1-CA68814 and P50-CA58204, awarded by the National Institutes of Health, and the United States government has certain rights in this invention.

BACKGROUND OF THE INVENTION

1. Field of the Invention

The present invention is directed to purified and isolated RTVP-1-GliPR-like polypeptides ("RGL polypeptides") and fragments thereof, the nucleic acids encoding such polypeptides, processes for production of recombinant forms of such polypeptides, antibodies generated against these polypeptides, fragmented peptides derived from these polypeptides, and uses thereof. In particular, the invention relates to compositions and methods for the detection, treatment and prevention of metastatic and other neoplastic disorders.

2. Description of Related Art

Cancer cells may be are defined by two heritable properties, uncontrolled growth and uncontrolled invasion of normal tissue. A cancerous cell can divide in defiance of the normal growth constraints in a cell leading to a localized growth or tumor. In addition, some cancer cells may become metastatic, gaining the ability to migrate away from their initial site and invade other tissues areas and types. It is the combination of these two features that make a cancer cell especially dangerous.

An isolated abnormal cell population that grows uncontrollably will give rise to a tumor or neoplasm. As long as the neoplasm remains non-invasively in a single location, it is said to be benign, and a complete cure may be expected by removing the mass surgically. A tumor or neoplasm is counted as a cancer if it is malignant, that is, if its cells have the ability to invade surrounding tissue. True malignancy begins when the cells cross the basal lamina and begin to invade the underlying connective tissue. Malignancy also occurs when the cells gain the ability to detach from the main tumor mass, enter the bloodstream or lymphatic vessels, and form secondary tumors or metastases at other sites in the body. The more widely a tumor metastasizes, the harder it is to eradicate and treat.

As determined from epidemiological and clinical studies, most cancers develop in slow stages from mildly benign into malignant neoplasms. Malignant cancer usually begins as a benign localized cell population with abnormal growth characteristics called dysplasia. The abnormal cells acquire abnormal growth characteristics resulting in a neoplasia characterized as a cell population of localized growth and swelling. If untreated, the neoplasia in situ may progress into a malignant neoplasia. Several years, or tens of years may elapse from the first sign of dysplasia to the onset of full blown malignant cancer. This characteristic process is observed in a number of cancers. Prostate cancer provides one of the clearest examples of the progression of normal tissue to benign neoplasm to malignant neoplasm.

Prostate cancer is the most common malignancy in men in the USA, resulting in an estimated 41,800 deaths in 1997. (Parker S L, et al., CA Cancer J Clin 47: 5-27, 1997). The widespread use of prostate-specific antigen (PSA) has dramatically increased the number of patients diagnosed with prostate cancer and generally lowered the stage of disease at diagnosis. (Scardino P T, Urol. Clin. N. Am. 16:635-655, 1989; Epstein J L, et al., JAMA 271: 368-374, 1994). Nevertheless, 5%-10% of cancers detected by PSA screening are clinically advanced and not candidates for radical prostatectomy. Despite surgical removal of the prostate, 30%-60% of men treated will have recurrence of cancer within 5 years, suggesting that the clinical stage of the patients undergoing surgery was highly inaccurate. 20%-57% of patients undergoing definitive surgery with presumed localized disease will have rising PSA following treatment, also indicative of local or distant residual disease. (Ohori M, et al., J. Urol. 154: 1818-1824, 1995; Zeitman A L, et al., Urology 43: 828-833, 1994). Neither of these conditions is amenable to curative therapy.

The walnut-sized prostate is an encapsulated organ of the mammalian male urogenital system. Located at the base of the bladder, the prostate is partitioned into zones referred to as the central, peripheral and transitional zones, all of which surround the urethra. Histologically, the prostate is a highly microvascularized gland comprising fairly large glandular spaces lined with epithelium which, along with the seminal vesicles, supply the majority of fluid to the male ejaculate. As an endocrine-dependent organ, the prostate responds to both the major male hormone, testosterone, and the major female hormones, estrogen and progesterone. Testicular androgen is considered important for prostate growth and development because, in both humans and other animals, castration leads to prostate atrophy and, in most cases, an absence of any incidence of prostatic carcinoma.

The major neoplastic disorders of the prostate are benign enlargement of the prostate, also called benign prostatic hyperplasia (BPH), and prostatic carcinoma, a type of neoplasia. BPH is very common in men over the age of 50. It is characterized by the presence of a number of large distinct nodules in the periurethral area of the prostate. Although benign and not malignant, these nodules can produce obstruction of the urethra causing nocturia, hesitancy to void, and difficulty in starting and stopping a urine stream upon voiding the bladder. Left untreated, a percentage of these prostate hyperplasias and neoplasias may develop into malignant prostatic carcinoma.

In its more aggressive form, malignant transformed prostatic tissues escape from the prostate capsule and metastasize invading locally and throughout the bloodstream and lymphatic system. Metastasis, defined as tumor implants which are discontinuous with the primary tumor, can occur through direct seeding, lymphatic spread and hematogenous spread. All three routes have been found to occur with prostatic carcinoma. Local invasion typically involves the seminal vesicles, the base of the urinary bladder, and the urethra. Direct seeding occurs when a malignant neoplasm penetrates a natural open field such as the peritoneal, pleural or pericardial cavities. Cells seed along the surfaces of various organs and tissues within the cavity or can simply fill the cavity spaces. Hematogenous spread is typical of sarcomas and carcinomas. Hematogenous spread of prostatic carcinoma occurs primarily to the bones, but can include massive visceral invasion as well. It has been estimated that about 60% of newly diagnosed prostate cancer patients will have metastases at the time of initial diagnosis.

Surgery or radiotherapy is the treatment of choice for early prostatic neoplasia. Surgery involves complete removal of the entire prostate (radical prostatectomy), and often removal of the surrounding lymph nodes, or lymphadenectomy. Radiotherapy, occasionally used as adjuvant therapy, may be either external or interstitial using 125I. Endocrine therapy is the treatment of choice for more advanced forms. The aim of this therapy is to deprive the prostate cells, and presumably the transformed prostate cells as well, of testosterone. This is accomplished by orchiectomy (castration) or administration of estrogens or synthetic hormones which are agonists of luteinizing hormone-releasing hormone. These cellular messengers directly inhibit testicular and organ synthesis and suppress luteinizing hormone secretion which in turn leads to reduced testosterone secretion by the testes. In normal prostate, removal of androgenic hormones results in regression of the gland involving apoptosis of more than 60% of the luminal epithelial cells. Although often initially sensitive to removal of androgens, prostate cancer cells eventually lose this response and continue to grow and spread even in the absence of androgenic steroids. Despite the advances made in achieving a pharmacologic orchiectomy, the survival rates for those with late stage carcinomas are rather bleak Current therapeutic regimens for metastatic disease typically involve both chemical and surgical androgen ablation, which although has been demonstrated to extend life when compared to untreated patients, almost invariably results in the development of hormone-refractory disease and the demise of the patient. The fundamental concepts upon which current androgen ablation therapy was developed were reported more than 50 years ago by Huggins and Hodges. (Huggins C, et al., Cancer Res. 1:293-297, 1941). These experiments reported the phenomenon in which removal of androgenic steroids by castration resulted in reduced growth and biochemical activities in prostate cancer.

With the advent of molecular biology, various investigators in laboratories have attempted to understand the molecular biology of castration-induced regression of the prostate at a more mechanistic level. The model systems selected almost invariably compared mRNAs produced prior to castration and during castration-induced regression using rat prostate model systems in vivo. These model systems yield gene activities that may be involved in castration-induced regression but could also be involved in activities that are not directly relevant or related to castration-induced regression but were stimulated by removal of androgenic steroids. It is anticipated that only a small fraction of gene activities modulated by steroid withdrawal would indeed be involved in castration-induced regression and, therefore, significant confounding background activity would be seen in these existing model systems. There is therefore a need for a model system in which the androgenic-stimulated gene activities not associated with castration-induced regression, or "background" gene activities, would be normalized. Moreover, a better understanding of the molecular basis of metastasis, in prostate cancer, as well as other forms of cancer, would allow rational efforts toward the development of novel effective anti-metastatic therapy to proceed.

One such advancement in the understanding of the molecular basis of prostate cancer has occurred through the study of p53. It has been shown that there exists a specific and established association between loss of p53 function and prostate cancer metastasis. Recent studies demonstrated that specific p53 mutations are clonally expanded in metastatic prostate cancer (Stapleton, A M. et al., Clin Cancer Res 3, 1389-97, 1997) and that a pattern of aberrant p53 expression in primary tumors, termed "clustered p53 staining," has significant prognostic value in predicting recurrence following radical prostatectomy (Quinn, D. I. et. al., Cancer Res 60, 1585-94, 2000 and Stapleton, A M. et. al., Cancer 82, 168-75, 1998). It is generally considered that the nature of functional alterations which occur in cells containing p53 mutations specifically facilitates metastatic seeding, survival, and growth at distant metastatic sites. These alterations likely result, in part, from aberrant regulation of genes under the transcriptional control of p53 that have previously been shown to mediate apoptosis (el-Deiry, W. S., Setnin Cancer Biol 8, 345-57, 1998; Miyashita, T. & Reed, S. C., Cell 80, 293-9, 1995; Sheikh, M S. et. al., Cancer Res 58, 1593-8, 1998; Oda, K. et. al., Cell 102, 849-62, 2000; and Zhu, J. & Chen, Mol Cell Biol 20, 5602-18, 2000) and anti-angiogenic activities (Dameron, K. M., Volpert, O. V., Tainsky, M. A. & Bouck, N., Science 265, 1582-4, 1994; Lopez-Ocejo, O. et. al., Oncogene 19, 4611-20, 2000; Zou, Z. et. al., J Biol Chem 275, 6051-4, 2000; Zhang, M., Volpert, O., Shi, Y. H. & Bouck, N., Nat Med 6, 196-9, 2000; and Zhang, Y., Griffith, E. C., Sage, S., Jacks, T. & Liu, J. O., Proc Natl Acad Sci USA 97, 6427-32, 2000).

Surprisingly, it has been discovered that certain proteins related to testes-specific, vespid and pathogenic proteins ("RTVP-related" or "RTVP-like" proteins), are up-regulated by p53 in mouse prostate cancer cells. Proteins which are Related to Testes-specific, Vespid and Pathogenic proteins include those proteins with homology to mammalian testes-specific proteins (e.g. TPXI), plant pathogenesis-related proteins (e.g. PR-protein such as subtype 1, PR-lb), vespid venom allergan proteins (antigen 5), or combinations thereof. Homology means that there is a relevant degree of similarity in the amino acid sequence between a polypeptide of the invention and one or more of the proteins mammalian testes-specific proteins, plant pathogenesis proteins and vespid venom allergan antigen 5, or in the respective gene sequences. Relevant homology means that the degree of amino acid sequence similarity is about 35% or greater, preferably about 45% or greater, more preferably about 60% or greater, and even more preferably about 75% or greater. Homology can be determined directly by sequencing the polypeptide of interest and comparing it with the known sequence, or experimentally by methods well know to those or ordinary skill in the art. Homology can be determined using, for example, blastp queries at default settings for amino acid homology determinations, and using blastn queries at default settings for nucleic acid homology determinations.

SUMMARY OF THE INVENTION

The invention aids in fulfilling these various needs in the art by providing isolated RTVP-related nucleic acids and polypeptides encoded by these nucleic acids. Particular embodiments of the invention are directed to an isolated "RGL" nucleic acid molecule ("RGL-alpha") comprising the DNA sequence of SEQ ID NO: 1 or an isolated alternate form ("RGL-beta") comprising the DNA sequence of SEQ ID NO: 3 as well as isolated RGL nucleic acid molecules encoding the amino acid sequence of SEQ ID NO: 2 or SEQ ID NO: 4, respectively, and nucleic acid molecules complementary to these sequences. Both single-stranded and double-stranded RNA and DNA nucleic acid molecules are encompassed by the invention, as well as nucleic acid molecules that hybridize to a denatured, double-stranded DNA comprising all or a portion of SEQ ID NO: 1 or 3. Also encompassed are isolated nucleic acid molecules that are derived by in vitro mutagenesis of nucleic acid molecules comprising sequences of SEQ ID NO: 1 or 3, that are degenerate from nucleic acid molecules comprising sequences of SEQ ID NO: 1 or 3, and that are allelic variants of DNA of the invention. The invention also encompasses recombinant vectors that direct the expression of these nucleic acid molecules and host cells stably or transiently transformed or transfected with these vectors.

In addition, the invention encompasses methods of using the nucleic acids noted above to identify nucleic acids encoding proteins having anti-neoplastic activity, especially with regard to genitourinary tumors, such as prostate and testicular cancers, or other human conditions associated with p53 activity.

The invention also encompasses the use of sense, antisense oligonucleotides or siRNA from the nucleic acid of SEQ ID NO: 1 or 3 to either increase or inhibit the expression of the polynucleotide encoded by the RGL gene.

The invention also encompasses isolated polypeptides and fragments thereof encoded by these nucleic acid molecules, including soluble or secreted polypeptide portions of SEQ ID No: 2 or 4. The invention further encompasses methods for the production of these polypeptides, including culturing a host cell under conditions promoting expression and recovering the polypeptide from the culture medium. Especially, the expression of these polypeptides in bacteria, yeast, plant, insect, and animal cells is encompassed by the invention.

In general, the polypeptides of the invention can be used to advance the diagnosis and treatment of conditions associated with the cellular processes of apoptosis and neoplasia. For example, the invention includes assays utilizing these polypeptides to screen for potential inhibitors of neoplastic activity associated with polypeptide counter-structure molecules, as well as methods of using these polypeptides as to study cellular processes associated with oncogenic diseases which may be modulated by RTVP-related polypeptide molecules. Further, methods of using these polypeptides in the design of inhibitors thereof are also an aspect of the invention.

Further encompassed by this invention are methods and compositions to aid in the detection and treatment of neoplastic disorders, especially genitourinary tumors, such as prostate and testicular cancers, including the use of the RGL promoter to drive the targeted expression of anti-neoplastic molecules.

Isolated polyclonal or monoclonal antibodies that bind to these RGL polypeptides are also encompassed by the invention, in addition the use of these antibodies to aid in purifying the polypeptides, as well as in the detection and treatment of neoplastic disorders.

BRIEF DESCRIPTION OF THE FIGURES

FIG. 1 presents the nucleotide sequences of RGL-alpha (SEQ ID No.: 1) and RGL-beta (SEQ ID No.: 3) in comparison to that of RTVP-1 and provides a consensus sequence.

FIG. 2 presents the amino acid sequences of RGL-alpha (SEQ ID No.: 2) and RGL-beta (SEQ ID No.: 4) in comparison to that of RTVP-1.

FIG. 3 presents the predicted p53 binding sites within the RGL1 promoter.

DETAILED DESCRIPTION OF THE INVENTION

Figure 4:
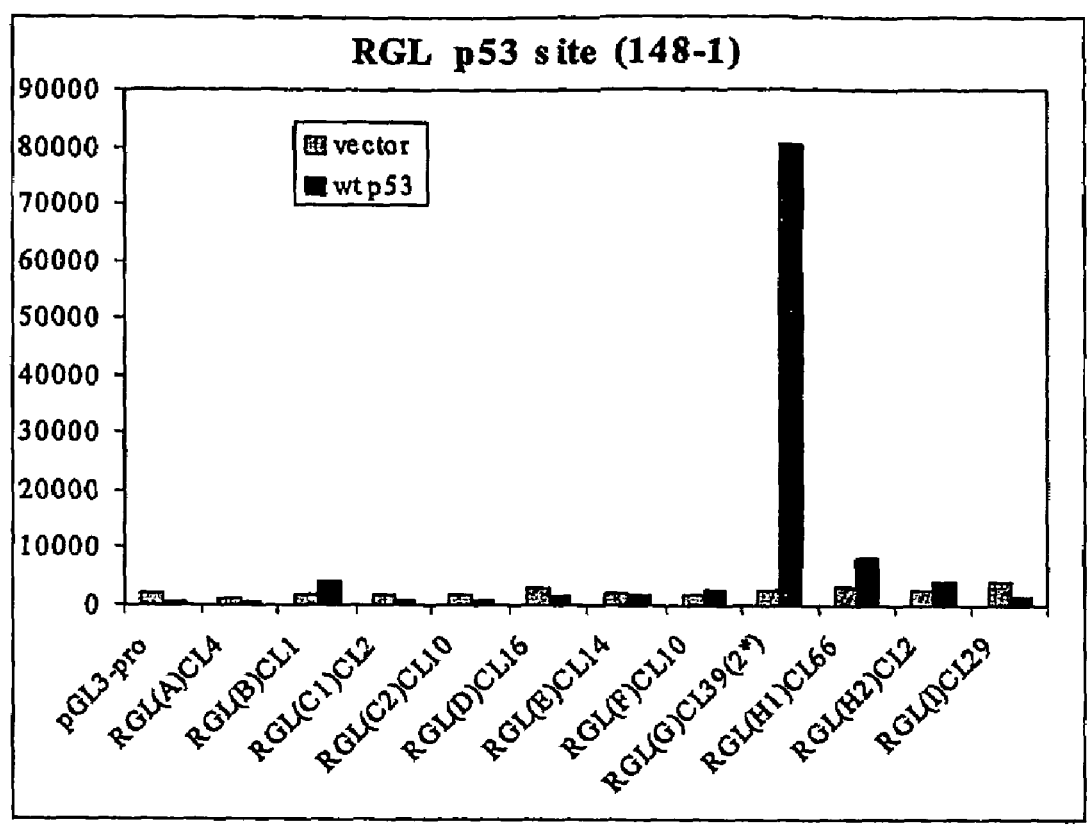
FIG. 4 demonstrates p53 binding to a nucleotide segment of the RGL1 promoter predicted to contain a p53 binding site.

The present disclosure arises from the surprising discovery of previously unknown splice variant of the RGL gene, RGL-beta, as well as the novel finding that both RGL-alpha and RGL-beta are capable of inducing apoptosis in and suppressing the cell growth of a cancerous prostate cell line.

The nucleic acid molecules encompassed in the invention include the following nucleotide sequences (shown in FIG. 1):

SEQ ID NO.: 1 representing the nucleotide sequence of RGL-alpha.

SEQ ID NO.: 3 representing the nucleotide sequence of RGL-beta.

The amino acid sequences of the polypeptides encoded by the nucleotide sequence of the invention includes (shown in FIG. 2):

SEQ ID NO.: 2 representing the amino acid sequence of RGL-alpha.

SEQ ID NO.: 4 representing the amino acid sequence of RGL-beta.

The discovery of the nucleic acids of the invention enables the construction of expression vectors comprising nucleic acid sequences encoding polypeptides; host cells transfected or transformed with the expression vectors; isolated and purified biologically active polypeptides and fragments thereof; the use of the nucleic acids or oligonucleotides thereof as probes to identify nucleic acid encoding proteins having anti-neoplastic activity, the use of the nucleic acids or oligonucleotides thereof to identify human chromosome number 12q on which the RGL gene is located, the use of the nucleic acids or oligonucleotides thereof to map genes on human chromosome number 12q, the use of the nucleic acids or oligonucleotides thereof to identify and treat certain diseases, syndromes or other human conditions associated neoplastic disorders, especially prostate cancer; the use of single-stranded sense or antisense oligonucleotides from the nucleic acids to inhibit expression of polynucleotide encoded by the RGL gene; the use of such polypeptides and soluble or secreted fragments to inhibit neoplastic activity(s); and the use of antibodies to purify RTVP-related polypeptides, especially RGL polypeptides or fragments thereof.

In a particular embodiment, the invention relates to certain isolated nucleotide sequences that are free from contaminating endogenous material. A "nucleotide sequence" refers to a polynucleotide molecule in the form of a separate fragment or as a component of a larger nucleic acid construct. The nucleic acid molecule has been derived from DNA or RNA isolated at least once in substantially pure form and in a quantity or concentration enabling identification, manipulation, and recovery of its component nucleotide sequences by standard biochemical methods (such as those outlined in Sambrook et al., *Molecular Cloning: A Laboratory Manual*, 2nd sed., Cold Spring Harbor Laboratory, Cold Spring Harbor, N.Y. (1989)). Such sequences are preferably provided and/or constructed in the form of an open reading frame uninterrupted by internal non-translated sequences, or introns, that are typically present in eukaryotic genes. Sequences of non-translated DNA can be present 5' or 3' from an open reading frame, where the same do not interfere with manipulation or expression of the coding region.

Nucleic acid molecules of the invention include DNA in both single-stranded and double-stranded form, as well as the corresponding complementary sequences. DNA includes, for example, cDNA, genomic DNA, chemically synthesized DNA, DNA amplified by PCR, and combinations thereof. Genomic DNA may be isolated by conventional techniques, e.g., using the cDNA of SEQ ID NO: 1 or 3, or a suitable fragment thereof, as a probe.

The DNA molecules of the invention include full length genes as well as polynucleotides and fragments thereof. Other embodiments include DNA encoding a soluble or secreted form, e.g., fragments comprising the extracellular domains of the protein, either with or without a signal peptide.

The nucleic acids of the invention are preferentially derived from human sources, but the invention includes those derived from non-human species, as well.

Preferred Sequences

A particularly preferred nucleotide sequence of the invention is SEQ ID NO: 1 or 3, as set forth in FIG. 1. The sequences of amino acids encoded by the DNA of SEQ ID NOs:1 and 3 are shown as SEQ ID NOs: 2 and 4, respectively, in FIG. 2. Based on homology parameters discussed above, the RGL polynucleotide is a member of the RTVP family containing p53 binding sites within its promotor, a signal peptide and two SGP-domains (small G protein).

Additional Sequences

Due to the known degeneracy of the genetic code, wherein more than one codon can encode the same amino acid, a DNA sequence can vary from that shown in SEQ ID NO: 1 or 3 and still encode a polypeptide having the amino acid sequence of SEQ ID NO: 2 or 4, respectively. Such variant DNA sequences can result from silent mutations (e.g. occurring during PCR amplification), or can be the product of deliberate mutagenesis of a native sequence.

The invention thus provides isolated DNA sequences encoding polypeptides of the invention, selected from: (a) DNA comprising the nucleotide sequence of SEQ ID NO: 1 or 3 (b) DNA encoding the polypeptides of SEQ ID NO: 2 or 4; (c) DNA capable of hybridization to a DNA of (a) or (b) under conditions of moderate stringency and which encodes polypeptides of the invention; (d) DNA capable of hybridization to a DNA of (a) or (b) under conditions of high stringency and which encodes polypeptides of the invention, and (e) DNA which is degenerate as a result of the genetic code to a DNA defined in (a), (b), (c), or (d) and which encode polypeptides of the invention. Of course, polypeptides encoded by such DNA sequences are encompassed by the invention.

The basic parameters affecting the choice of hybridization conditions and guidance for devising suitable conditions are set forth by Sambrook et al., 1989. As used herein, conditions of moderate stringency can be readily determined by those having ordinary skill in the art based on, for example, the length and/or base composition of the DNA. For hybridizing probes longer than about 100 nucleotides with filter-bound target DNA or RNA, one way of achieving moderately stringent conditions involves the use of a prewashing solution containing 5×SSC, 0.5% SDS, 1.0 mM EDTA (pH 8.0), hybridization buffer of about 50% formamide, 6×SSC, and a hybridization temperature of about 42° C. (or other similar hybridization solutions, such as one containing about 50% formamide, with a hybridization temperature of about 42° C.), and washing conditions of about 60° C., in 0.5×SSC, 0.1% SDS. Conditions of high stringency can also be readily determined by the skilled artisan based on, for example, the length and base composition of the DNA. Generally, such conditions are defined as hybridization conditions as above, but with washing at approximately 68° C., 0.2×SSC, 0.1% SDS. It should be understood that the wash temperature and wash salt concentration can be adjusted as necessary to achieve a desired degree of stringency by applying the basic principles that govern hybridization reactions and duplex stability, as known to those skilled in the art (see, e.g., Sambrook et al., 1989). It should be further understood that hybridization conditions for oligonucleotide probes of defined length and sequence can be designed by applying formulae known in the art (e.g., see Sambrook et al., 1989, at 11.45-11.47).

Also included as an embodiment of the invention is DNA encoding polypeptide fragments and polypeptides comprising conservative amino acid substitution(s), as described below.

In another embodiment, the nucleic acid molecules of the invention also comprise nucleotide sequences that are at least 80% identical to a native sequence. Also contemplated are embodiments in which a nucleic acid molecule comprises a sequence that is at least 90% identical, at least 95% identical, at least 98% identical, at least 99% identical, or at least 99.9% identical to a native sequence.

The percent identity may be determined by visual inspection and mathematical calculation. Alternatively, the percent identity of two nucleic acid sequences can be determined by comparing sequence information using the GAP computer program, version 6.0 described by Devereux et al. (*Nucl. Acids Res.* 12:387, 1984) and available from the University of Wisconsin Genetics Computer Group (UWGCG). The preferred default parameters for the GAP program include: (1) a unary comparison matrix (containing a value of 1 for identities and 0 for non-identities) for nucleotides, and the weighted comparison matrix of Gribskov and Burgess, *Nucl. Acids Res.* 14:6745, 1986, as described by Schwartz and Dayhoff, eds., *Atlas of Protein Sequence and Structure*, National Biomedical Research Foundation, pp. 353-358, 1979; (2) a penalty of 3.0 for each gap and an additional 0.10 penalty for each symbol in each gap; and (3) no penalty for end gaps. Other programs used by one skilled in the art of sequence comparison may also be used.

The invention also provides isolated nucleic acids useful in the production of polypeptides. Such polypeptides may be prepared by any of a number of conventional techniques. A DNA sequence encoding a RGL (alpha or beta) polypeptide, or desired fragment thereof may be subcloned into an expression vector for production of the polypeptide or fragment. The DNA sequence advantageously is fused to a sequence encoding a suitable leader or signal peptide. Alternatively, the desired fragment may be chemically synthesized using known techniques. DNA fragments also may be produced by restriction endonuclease digestion of a full length cloned DNA sequence, and isolated by electrophoresis on agarose gels. If necessary, oligonucleotides that reconstruct the 5' or 3' terminus to a desired point may be ligated to a DNA fragment generated by restriction enzyme digestion. Such oligonucleotides may additionally contain a restriction endonuclease cleavage site upstream of the desired coding sequence, and position an initiation codon (ATG) at the N-terminus of the coding sequence.

The well-known polymerase chain reaction (PCR) procedure also may be employed to isolate and amplify a DNA sequence encoding a desired protein fragment. Oligonucleotides that define the desired termini of the DNA fragment are employed as 5' and 3' primers. The oligonucleotides may additionally contain recognition sites for restriction endonucleases, to facilitate insertion of the amplified DNA fragment into an expression vector. PCR techniques are described in Saiki et al., *Science* 239:487 (1988); *Recombinant DNA Methodology*, Wu et al., eds., Academic Press, Inc., San Diego (1989), pp. 189-196; and *PCR Protocols: A Guide to Methods and Applications*, Innis et al., eds., Academic Press, Inc. (1990).

Polypeptides and Fragments Thereof

The invention encompasses polypeptides and fragments thereof in various forms, including those that are naturally occurring or produced through various techniques such as procedures involving recombinant DNA technology. Such forms include, but are not limited to, derivatives, variants, and oligomers, as well as fusion proteins or fragments thereof.

Polypeptides and Fragments Thereof

The polypeptides of the invention include full length proteins encoded by the nucleic acid sequences set forth above. Particularly preferred polypeptides comprise the amino acid sequence of SEQ ID NO: 2 or 4 with particularly preferred fragments comprising amino acids 105 to 113 of SEQ ID NO: 4.

The polypeptides of the invention may be membrane bound or they may be secreted and thus soluble. Soluble polypeptides are capable of being secreted from the cells in which they are expressed. In general, soluble polypeptides may be identified (and distinguished from non-soluble membrane-bound counterparts) by separating intact cells which express the desired polypeptide from the culture medium, e.g., by centrifugation, and assaying the medium (supernatant) for the presence of the desired polypeptide. The presence of polypeptide in the medium indicates that the polypeptide was secreted from the cells and thus is a soluble form of the protein.

In one embodiment, the soluble polypeptides and fragments thereof comprise all or part of the extracellular domain, but lack the transmembrane region that would cause retention of the polypeptide on a cell membrane. A soluble polypeptide may include the cytoplasmic domain, or a portion thereof, as long as the polypeptide is secreted from the cell in which it is produced.

In general, the use of soluble forms is advantageous for certain applications. Purification of the polypeptides from recombinant host cells is facilitated, since the soluble polypeptides are secreted from the cells. Further, soluble polypeptides are generally more suitable for therapeutic or research based intravenous administration.

The invention also provides polypeptides and fragments of the extracellular domain that retain a desired biological activity, preferably anti-neoplastic activities (including altering cytokine and chemokine levels) for which assays for identifying are well known in the art. Such a fragments may be a soluble polypeptide, as described above. In another embodiment, the polypeptides and fragments advantageously include regions that are conserved in the RGL or RTVP family as described above.

Also provided herein are polypeptide fragments comprising at least 20, or at least 30, contiguous amino acids of the sequence of SEQ ID NO: 2 or 4.

Variants

Naturally occurring variants as well as derived variants of the polypeptides and fragments are provided herein. Variants may exhibit amino acid sequences that are at least 80% identical. Also contemplated are embodiments in which a polypeptide or fragment comprises an amino acid sequence that is at least 90% identical, at least 95% identical, at least 98% identical, at least 99% identical, or at least 99.9% identical to the preferred polypeptide or fragment thereof. Percent identity may be determined by visual inspection and mathematical calculation. Alternatively, the percent identity of two protein sequences can be determined by comparing sequence information using the GAP computer program, based on the algorithm of Needleman and Wunsch (J. Mol. Bio. 48:443, 1970) and available from the University of Wisconsin Genetics Computer Group (UWGCG). The preferred default parameters for the GAP program include: (1) a scoring matrix, blosum62, as described by Henikoff and Henikoff (Proc. Natl. Acad. Sci. USA 89:10915, 1992); (2) a gap weight of 12; (3) a gap length weight of 4; and (4) no penalty for end gaps. Other programs used by one skilled in the art of sequence comparison may also be used.

The variants of the invention include, for example, those that result from alternate mRNA splicing events or from proteolytic cleavage. For example, RGL-beta contains an additional 9 amino acid insertion (amino acids 105-113 of SEQ ID NO.: 4; TPQLIIPNQ), as compared to RGL-alpha, that likely results from an alternate splicing event. Alternate splicing of mRNA, for example, may also yield a truncated but biologically active protein, such as a naturally occurring soluble form of the protein. Variations attributable to proteolysis include, for example, differences in the N- or C-termini upon expression in different types of host cells, due to proteolytic removal of one or more terminal amino acids from the protein (generally from 1-5 terminal amino acids). Proteins in which differences in amino acid sequence are attributable to genetic polymorphism (allelic variation among individuals producing the protein) are also contemplated herein.

Additional variants within the scope of the invention include polypeptides that may be modified to create derivatives thereof by forming covalent or aggregative conjugates with other chemical moieties, such as glycosyl groups, lipids, phosphate, acetyl groups and the like. Covalent derivatives may be prepared by linking the chemical moieties to functional groups on amino acid side chains or at the N-terminus or C-terminus of a polypeptide. Conjugates comprising diagnostic (detectable) or therapeutic agents attached thereto are contemplated herein, as discussed in more detail below.

Other derivatives include covalent or aggregative conjugates of the polypeptides with other proteins or polypeptides, such as by synthesis in recombinant culture as N-terminal or C-terminal fusions. Examples of fusion proteins are discussed below in connection with oligomers. Further, fusion proteins can comprise peptides added to facilitate purification and identification. Such peptides include, for example, poly-His or the antigenic identification peptides described in U.S. Pat. No. 5,011,912 and in Hopp et al., *Bio/Technology* 6:1204, 1988. One such peptide is the FLAG® peptide, Asp-Tyr-Lys-Asp-Asp-Asp-Asp-Lys, which is highly antigenic and provides an epitope reversibly bound by a specific monoclonal antibody, enabling rapid assay and facile purification of expressed recombinant protein. A murine hybridoma designated 4E11 produces a monoclonal antibody that binds the FLAG® peptide in the presence of certain divalent metal cations, as described in U.S. Pat. No. 5,011,912, hereby incorporated by reference. The 4E11 hybridoma cell line has been deposited with the American Type Culture Collection under accession no. HB 9259. Monoclonal antibodies that bind the FLAG® peptide are available from Eastman Kodak Co., Scientific Imaging Systems Division, New Haven, Conn.

Among the variant polypeptides provided herein are variants of native polypeptides that retain the native biological activity or the substantial equivalent thereof. One example is a variant that binds with essentially the same binding affinity as does the native form. Binding affinity can be measured by conventional procedures, e.g., as described in U.S. Pat. No. 5,512,457 and as set forth below.

Variants include polypeptides that are substantially homologous to the native form, but which have an amino acid sequence different from that of the native form because of one or more deletions, insertions or substitutions. Particular embodiments include, but are not limited to, polypeptides that comprise from one to ten deletions, insertions or substitutions of amino acid residues, when compared to a native sequence.

A given amino acid may be replaced, for example, by a residue having similar physiochemical characteristics. Examples of such conservative substitutions include substitution of one aliphatic residue for another, such as Ile, Val, Leu, or Ala for one another; substitutions of one polar residue for another, such as between Lys and Arg, Glu and Asp, or Gln and Asn; or substitutions of one aromatic residue for another, such as Phe, Trp, or Tyr for one another. Other conservative substitutions, e.g., involving substitutions of entire regions having similar hydrophobicity characteristics, are well known.

Similarly, the DNAs of the invention include variants that differ from a native DNA sequence because of one or more deletions, insertions or substitutions, but that encode a biologically active polypeptide.

Production of Polypeptides and Fragments Thereof

Expression, isolation and purification of the polypeptides and fragments of the invention may be accomplished by any suitable technique, including but not limited to the following:

Expression Systems

The present invention also encompasses recombinant cloning and expression vectors containing DNA, as well as host cell containing the recombinant vectors. Expression vectors comprising DNA may be used to prepare the polypeptides or fragments of the invention encoded by the DNA. A method for producing polypeptides comprises culturing host cells transformed with a recombinant expression vector encoding the polypeptide, under conditions that promote expression of the polypeptide, then recovering the expressed polypeptides from the culture. The skilled artisan will recognize that the procedure for purifying the expressed polypeptides will vary according to such factors as the type of host cells employed, and whether the polypeptide is membrane-bound or a soluble form that is secreted from the host cell.

Any suitable expression system may be employed. The vectors include a DNA encoding a polypeptide or fragment of the invention, operably linked to suitable transcriptional or translational regulatory nucleotide sequences, such as those derived from a mammalian, microbial, viral, or insect gene. Examples of regulatory sequences include transcriptional promoters, operators, or enhancers, an mRNA ribosomal binding site, and appropriate sequences which control transcription and translation initiation and termination. Nucleotide sequences are operably linked when the regulatory sequence functionally relates to the DNA sequence. Thus, a promoter nucleotide sequence is operably linked to a DNA sequence if the promoter nucleotide sequence controls the transcription of the DNA sequence. An origin of replication that confers the ability to replicate in the desired host cells, and a selection gene by which transformants are identified, are generally incorporated into the expression vector.

In addition, a sequence encoding an appropriate signal peptide (native or heterologous) can be incorporated into expression vectors. A DNA sequence for a signal peptide (secretory leader) may be fused in frame to the nucleic acid sequence of the invention so that the DNA is initially transcribed, and the mRNA translated, into a fusion protein comprising the signal peptide. A signal peptide that is functional in the intended host cells promotes extracellular secretion of the polypeptide. The signal peptide is cleaved from the polypeptide upon secretion of polypeptide from the cell.

The skilled artisan will also recognize that the position(s) at which the signal peptide is cleaved may differ from that predicted by computer program, and may vary according to such factors as the type of host cells employed in expressing a recombinant polypeptide. A protein preparation may include a mixture of protein molecules having different N-terminal amino acids, resulting from cleavage of the signal peptide at more than one site.

Suitable host cells for expression of polypeptides include prokaryotes, yeast or higher eukaryotic cells. Mammalian or insect cells are generally preferred for use as host cells. Appropriate cloning and expression vectors for use with bacterial, fungal, yeast, and mammalian cellular hosts are described, for example, in Pouwels et al. *Cloning Vectors: A Laboratory Manual*, Elsevier, N.Y., (1985). Cell-free translation systems could also be employed to produce polypeptides using RNAs derived from DNA constructs disclosed herein.

Isolation and Purification

The invention also includes methods of isolating and purifying the polypeptides and fragments thereof.

The "isolated" polypeptides or fragments thereof encompassed by this invention are polypeptides or fragments that are not in an environment identical to an environment in which it or they can be found in nature. The "purified" polypeptides or fragments thereof encompassed by this invention may be essentially free of association with other proteins or polypeptides, for example, as a purification product of recombinant expression systems such as those described above or as a purified product from a non-recombinant source such as naturally occurring cells and/or tissues.

In one preferred embodiment, the purification of recombinant polypeptides or fragments can be accomplished using fusions of polypeptides or fragments of the invention to another polypeptide to aid in the purification of polypeptides or fragments of the invention. Such fusion partners can include the poly-His or other antigenic identification peptides, as well as the Fc moieties.

With respect to any type of host cell, as is known to the skilled artisan, procedures for purifying a recombinant polypeptide or fragment will vary according to such factors as the type of host cells employed and whether or not the recombinant polypeptide or fragment is secreted into the culture medium.

In general, the recombinant polypeptide or fragment can be isolated from the host cells if not secreted, or from the medium or supernatant if soluble and secreted, followed by one or more concentration, salting-out, ion exchange, hydrophobic interaction, affinity purification or size exclusion chromatography steps. As to specific ways to accomplish these steps, the culture medium first can be concentrated using a commercially available protein concentration filter, for example, an Amicon or Millipore Pellicon ultrafiltration unit Following the concentration step, the concentrate can be applied to a purification matrix such as a gel filtration medium. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. In addition, a chromatofocusing step can be employed. Alternatively, a hydrophobic interaction chromatography step can be employed. Suitable matrices can be phenyl or octyl moieties bound to resins. In addition, affinity chromatography with a matrix which selectively binds the recombinant protein can be employed. Examples of such resins employed are lectin columns, dye columns, and metal-chelating columns. Finally, one or more reversed-phase high performance liquid chromatography (RP-HPLC) steps employing hydrophobic RP-HPLC media, (e.g., silica gel or polymer resin having pendant methyl, octyl, octyldecyl or other aliphatic groups) can be employed to further purify the polypeptides. Some or all of the foregoing purification steps, in various combinations, are well known and can be employed to provide an isolated and purified recombinant protein.

It is also possible to utilize an affinity column comprising a polypeptide-binding protein of the invention, such as a monoclonal antibody generated against polypeptides of the invention, to affinity-purify expressed polypeptides. These polypeptides can be removed from an affinity column using conventional techniques, e.g., in a high salt elution buffer and then dialyzed into a lower salt buffer for use or by changing pH or other components depending on the affinity matrix utilized, or be competitively removed using the naturally occurring substrate of the affinity moiety, such as a polypeptide derived from the invention.

In this aspect of the invention, polypeptide-binding proteins, such as the anti-polypeptide antibodies of the invention or other proteins that may interact with the polypeptide of the invention, can be bound to a solid phase support such as a column chromatography matrix or a similar substrate suitable for identifying, separating, or purifying cells that express polypeptides of the invention on their surface. Adherence of polypeptide-binding proteins of the invention to a solid phase contacting surface can be accomplished by any means, for example, magnetic microspheres can be coated with these polypeptide-binding proteins and held in the incubation vessel through a magnetic field. Suspensions of cell mixtures are contacted with the solid phase that has such polypeptide-binding proteins thereon. Cells having polypeptides of the invention on their surface bind to the fixed polypeptide-binding protein and unbound cells then are washed away. This affinity-binding method is useful for purifying, screening, or separating such polypeptide-expressing cells from solution. Methods of releasing positively selected cells from the solid phase are known in the art and encompass, for example, the use of enzymes. Such enzymes are preferably non-toxic and non-injurious to the cells and are preferably directed to cleaving the cell-surface binding partner.

Alternatively, mixtures of cells suspected of containing polypeptide-expressing cells of the invention first can be incubated with a biotinylated polypeptide-binding protein of the invention. Incubation periods are typically at least one hour in duration to ensure sufficient binding to polypeptides of the invention. The resulting mixture then is passed through a column packed with avidin-coated beads, whereby the high affinity of biotin for avidin provides the binding of the polypeptide-binding cells to the beads. Use of avidin-coated beads is known in the art. See Berenson, et al. *J. Cell. Biochem.*, 10D:239 (1986). Wash of unbound material and the release of the bound cells is performed using conventional methods.

The desired degree of purity depends on the intended use of the protein. A relatively high degree of purity is desired when the polypeptide is to be administered in vivo, for example. In such a case, the polypeptides are purified such that no protein bands corresponding to other proteins are detectable upon analysis by SDS-polyacrylamide gel electrophoresis (SDS-PAGE). It will be recognized by one skilled in the pertinent field that multiple bands corresponding to the polypeptide may be visualized by SDS-PAGE, due to differential glycosylation, differential post-translational processing, and the like. Most preferably, the polypeptide of the invention is purified to substantial homogeneity, as indicated by a single protein band upon analysis by SDS-PAGE. The protein band may be visualized by silver staining, Coomassie blue staining, or (if the protein is radiolabeled) by autoradiography.

Assays

The purified polypeptides of the invention (including proteins, polypeptides, fragments, variants, oligomers, and other forms) may be tested for the ability to bind counter-structures/ligands in any suitable assay, such as a conventional binding assay.

Use of RGL Nucleic Acid or Oligonucleotides

In addition to being used to express polypeptides as described above, the nucleic acids of the invention, including DNA, and oligonucleotides thereof can be used:

as probes to identify nucleic acid encoding proteins having anti-neoplastic activities;

as single-stranded sense or antisense oligonucleotides, to inhibit expression of polypeptide encoded by the RGL gene;

to help detect defective genes in an individual; and for preventative and therapeutic measures.

Probes

Among the uses of nucleic acids of the invention is the use of fragments as probes or primers. Such fragments generally comprise at least about 17 contiguous nucleotides of a DNA sequence. In other embodiments, a DNA fragment comprises at least 30, or at least 60, contiguous nucleotides of a DNA sequence.

Because homologs of SEQ ID NO: 1 or 3, from other mammalian species are contemplated herein, probes based on the human DNA sequence of SEQ ID NO: 1 or 3 may be used to screen cDNA libraries derived from other mammalian species, using conventional cross-species hybridization techniques.

Using knowledge of the genetic code in combination with the amino acid sequences set forth above, sets of degenerate oligonucleotides can be prepared. Such oligonucleotides are useful as primers, e.g., in polymerase chain reactions (PCR), whereby DNA fragments are isolated and amplified.

Sense-Antisense

Other useful fragments of the nucleic acids include antisense or sense oligonucleotides comprising a single-stranded nucleic acid sequence (either RNA or DNA) capable of binding to target mRNA (sense) or DNA (antisense) sequences. Antisense or sense oligonucleotides, according to the present invention, comprise a fragment of DNA (SEQ ID NO: 1 or 3). Such a fragment generally comprises at least about 14 nucleotides, preferably from about 14 to about 30 nucleotides. The ability to derive an antisense or a sense oligonucleotide, based upon a cDNA sequence encoding a given protein is described in, for example, Stein and Cohen (*Cancer Res.* 48:2659, 1988) and van der Krol et al. (*BioTechniques* 6:958, 1988).

Binding of antisense or sense oligonucleotides to target nucleic acid sequences results in the formation of duplexes that block or inhibit protein expression by one of several means, including enhanced degradation of the mRNA by RNAseH, inhibition of splicing, premature termination of transcription or translation, or by other means. The antisense oligonucleotides thus may be used to block expression of proteins. Antisense or sense oligonucleotides further comprise oligonucleotides having modified sugar-phosphodiester backbones (or other sugar linkages, such as those described in WO91/06629) and wherein such sugar linkages are resistant to endogenous nucleases. Such oligonucleotides with resistant sugar linkages are stable in vivo (i.e., capable of resisting enzymatic degradation) but retain sequence specificity to be able to bind to target nucleotide sequences.

Other examples of sense or antisense oligonucleotides include those oligonucleotides which are covalently linked to organic moieties, such as those described in WO 90/10448, and other moieties that increases affinity of the oligonucleotide for a target nucleic acid sequence, such as poly-(L-lysine). Further still, intercalating agents, such as ellipticine, and alkylating agents or metal complexes may be attached to sense or antisense oligonucleotides to modify binding specificities of the antisense or sense oligonucleotide for the target nucleotide sequence.

Antisense or sense oligonucleotides may be introduced into a cell containing the target nucleic acid sequence by any gene transfer method, including, for example, lipofection, $CaPO_4$-mediated DNA transfection, electroporation, or by using gene transfer vectors such as Epstein-Barr virus.

Sense or antisense oligonucleotides also may be introduced into a cell containing the target nucleotide sequence by formation of a conjugate with a ligand binding molecule, as described in WO 91/04753. Suitable ligand binding molecules include, but are not limited to, cell surface receptors, growth factors, other cytokines, or other ligands that bind to cell surface receptors. Preferably, conjugation of the ligand binding molecule does not substantially interfere with the ability of the ligand binding molecule to bind to its corresponding molecule or receptor, or block entry of the sense or antisense oligonucleotide or its conjugated version into the cell.

Alternatively, a sense or an antisense oligonucleotide may be introduced into a cell containing the target nucleic acid sequence by formation of an oligonucleotide-lipid complex, as described in WO 90/10448. The sense or antisense oligonucleotide-lipid complex is preferably dissociated within the cell by an endogenous lipase.

Preventative and Therapeutic Measures

The invention encompasses the use of RGL nucleic acids or fragments thereof in the prevention and treatment of neoplastic disorders. Nucleic acids of the invention may be packaged in a viral vector such as, for example, a retroviral, a vaccinia or an adenoviral vector and used in gene therapy. The invention further includes vectors comprising the nucleic acid sequences of the invention, polypeptides expressed by these vectors, and recombinant cells comprising these vectors.

The invention further provides for the use of RGL promoters which modulate transcription (e.g. by differential methylation of promoter sequences) of RGL sequences in normal, pre-malignant and malignant cell. These promoters can be functionally coupled to anti-neoplastic genes to treat or prevent cell proliferative disorders such as, for example, tumors, prostate cancer, and metastatic disease.

Nucleic acids and polypeptides of the invention may also be used as a diagnostic or therapeutic tools in the detection, treatment or prevention of diseases, such as neoplastic disorders (e.g. malignant tumors, metastatic disease) and cell or tissue growth disorders. For example the invention encompasses diagnostic aids or kits for the detection of neoplasia in a patient. Detection kits may comprise RGL nucleic acid sequences or (polypeptides) whose presence or absence in the sample would be indicative of the presence of a disease such as, for example, genitourinary cancer or a genitourinary metastasis, samples which can be analyzed include samples of biological fluids (e.g. blood, plasma, interstitial fluid, urine, cerebrospinal fluid) and samples of biological tissue (e.g. surgical biopsy). Treatment may involve using the sequences, or effective parts thereof, in gene therapy, including gene ablation, gene expression and gene suppression, such as antisense suppression. Diagnosis may involve genotypic analysis of samples to determine the existence and expression levels of the genes. Nucleic acids of the present invention may be used in various treatment and research modalities, including gene replacement, gene supplementation/over-expression, gene targeting, antisense inhibition, antisense blocking, genetic ablation and gene silencing. Gene replacement involves replacing a copy of a defective gene with another copy by homologous recombination. Gene supplementation involves placing a natively expressed gene under the control of a more prolific promoter system to increase the transcription of the gene as compared to its native state. Gene targeting involves the disruption of a cellular copy of a gene by homologous recombination. Gene targeting refers to a process of introducing a nucleic acid construct into a cell to specifically recombine with a target gene in the cell. The nucleic acid construct inactivates the gene after targeting. Inactivation may be by introduction of termination codons into a coding region or introduction of a repression site into a regulatory sequence. Antisense inhibition exploits the specificity of hybridization reactions between two complementary nucleic acid chains to suppress gene expression. Genetic ablation (gene knockout) may be performed after a cell is selected for use or by selecting a cell already comprising a genotype with the proper genetic ablation. Gene silencing is performed by transfecting cells with nucleic acids which cause genetic ablation or by antisense suppression. The silencing process may include processes such as gene targeting or antisense blocking.

Use of RGL Polypeptides and Fragmented Polypeptides
  Uses include, but are not limited to, the following:
  Purifying proteins and measuring activity thereof.
  Therapeutic and Research Reagents
  Preparation of Antibodies
  Purification Reagents The polypeptides of the invention finds use as a protein purification reagent. The polypeptides may be attached to a solid support material and used to purify binding partner(s) proteins by affinity chromatography. In particular embodiments, a polypeptide (in any form described herein that is capable of binding binding partner(s)) is attached to a solid support by conventional procedures. As one example, chromatography columns containing functional groups that will react with functional groups on amino acid side chains of proteins are available (Pharmacia Biotech, Inc., Piscataway, N.J.). In an alternative, a polypeptide/Fc protein (as discussed above) is attached to Protein A- or Protein G-containing chromatography columns through interaction with the Fc moiety.

The polypeptide also finds use in purifying or identifying cells that express binding partners (RGL ligands) on the cell surface. Polypeptides are bound to a solid phase such as a column chromatography matrix or a similar suitable substrate. For example, magnetic microspheres can be coated with the polypeptides and held in an incubation vessel through a magnetic field. Suspensions of cell mixtures containing putative RGL ligand expressing cells are contacted with the solid phase having the polypeptides thereon. Cells expressing binding partners on the cell surface bind to the fixed polypeptides, and unbound cells then are washed away.

Alternatively, the polypeptides can be conjugated to a detectable moiety, then incubated with cells to be tested for expression of RGL ligands. After incubation, unbound labeled matter is removed and the presence or absence of the detectable moiety on the cells is determined.

In a further alternative, mixtures of cells suspected of containing RGL ligand expressing cells are incubated with biotinylated polypeptides. Incubation periods are typically at least one hour in duration to ensure sufficient binding. The resulting mixture then is passed through a column packed with avidin-coated beads, whereby the high affinity of biotin for avidin provides binding of the desired cells to the beads. Procedures for using avidin-coated beads are known (see Berenson, et al. *J. Cell. Biochem.*, 10D:239, 1986). Washing to remove unbound material, and the release of the bound cells, are performed using conventional methods.

Measuring Activity

Polypeptides also find use in measuring the biological activity of RGL ligands in terms of their binding affinity. The polypeptides thus may be employed by those conducting "quality assurance" studies, e.g., to monitor shelf life and stability of protein under different conditions. For example, the polypeptides may be employed in a binding affinity study to measure the biological activity of a RGL ligand that has been stored at different temperatures, or produced in different cell types. The proteins also may be used to determine whether biological activity is retained after modification of a binding partner protein (e.g., chemical modification, truncation, mutation, etc.). The binding affinity of the modified binding partner protein is compared to that of an unmodified protein to detect any adverse impact of the modifications on biological activity of the modified one.

Therapeutic Agents

Polypeptides of the invention may be used in developing treatments for any neoplastic disorder mediated (directly or indirectly) by defective, or insufficient amounts of the polypeptides. These polypeptides may be administered to a mammal afflicted with such a neoplastic disorder, especially with regard to prostate cancer.

The polypeptides may also be employed in inhibiting neoplastic biological activities, in in vitro or in vivo procedures. For example, a purified polypeptide may be used to mimic binding to RGL ligands on endogenous cell surfaces. Biological effects that result from the binding to endogenous receptors thus are activated.

Compositions of the present invention may contain a polypeptide in any form described herein, such as native proteins, variants, derivatives, oligomers, and biologically active fragments. In particular embodiments, the composition comprises a soluble polypeptide or an oligomer comprising soluble RGL polypeptides.

Compositions comprising an effective amount of a polypeptide of the present invention, in combination with other components such as a physiologically acceptable diluent, carrier, or excipient, are provided herein. The polypeptides can be formulated according to known methods used to prepare pharmaceutically useful compositions. They can be combined in admixture, either as the sole active material or with other known active materials suitable for a given indication, with pharmaceutically acceptable diluents (e.g., saline, Tris-HCl, acetate, and phosphate buffered solutions), preservatives (e.g., thimerosal, benzyl alcohol, parabens), emulsifiers, solubilizers, adjuvants and/or carriers. Suitable formulations for pharmaceutical compositions include those described in *Remington's Pharmaceutical Sciences,* 16th ed. 1980, Mack Publishing Company, Easton, Pa.

In addition, such compositions can be complexed with polyethylene glycol (PEG), metal ions, or incorporated into polymeric compounds such as polyacetic acid, polyglycolic acid, hydrogels, dextran, etc., or incorporated into liposomes, microemulsions, micelles, unilamellar or multilamellar vesicles, erythrocyte ghosts or spheroblasts. Such compositions will influence the physical state, solubility, stability, rate of in vivo release, and rate of in vivo clearance, and are thus chosen according to the intended application.

The compositions of the invention can be administered in any suitable manner, e.g., topically, parenterally, or by inhalation. The term "parenteral" includes injection, e.g., by subcutaneous, intravenous, or intramuscular routes, also including localized administration, e.g., at a site of disease or injury. Sustained release from implants is also contemplated. One skilled in the pertinent art will recognize that suitable dosages will vary, depending upon such factors as the nature of the disorder to be treated, the patient's body weight, age, and general condition, and the route of administration. Preliminary doses can be determined according to animal tests, and the scaling of dosages for human administration is performed according to art-accepted practices.

Research Agents

Another embodiment of the invention relates to uses of RGL peptides to study cell signal transduction. For example Apoptosis, a biological activity moderated by RGL (FIG. 5), may play a central role in anti-neoplastic biological activities. Alternatively, RGL peptides may be use in the search for RGL ligands as discussed above.

Another use of the polypeptides of the present invention would be as a research tool for studying anti-neoplastic activities, especially with regard to genitourinary cancers.

Antibodies

Antibodies that are immunoreactive with the polypeptides of the invention are provided herein. Such antibodies specifically bind to the polypeptides via the antigen-binding sites of the antibody (as opposed to non-specific binding). Thus, the polypeptides, fragments, variants, fusion proteins, etc., as set forth above may be employed as "immunogens" in producing antibodies immunoreactive therewith. More specifically, the polypeptides, fragment, variants, fusion proteins, etc. contain antigenic determinants or epitopes that elicit the formation of antibodies.

These antigenic determinants or epitopes can be either linear or conformational (discontinuous). Linear epitopes are composed of a single section of amino acids of the polypeptide, while conformational or discontinuous epitopes are composed of amino acids sections from different regions of the polypeptide chain that are brought into close proximity upon protein folding (C. A. Janeway, Jr. and P. Travers, *Immuno Biology* 3:9 (Garland Publishing Inc., 2nd ed. 1996)). Because folded proteins have complex surfaces, the number of epitopes available is quite numerous; however, due to the conformation of the protein and steric hinderances, the number of antibodies that actually bind to the epitopes is less than the number of available epitopes (C. A. Janeway, Jr. and P. Travers, *Immuno Biology* 2:14 (Garland Publishing Inc., 2nd ed. 1996)). Epitopes may be identified by any of the methods known in the art.

Thus, one aspect of the present invention relates to the antigenic epitopes of the polypeptides of the invention. Such epitopes are useful for raising antibodies, in particular monoclonal antibodies, as described in more detail below. Additionally, epitopes from the polypeptides of the invention can be used as research reagents, in assays, and to purify specific binding antibodies from substances such as polyclonal sera or supernatants from cultured hybridomas. Such epitopes or variants thereof can be produced using techniques well known in the art such as solid-phase synthesis, chemical or enzymatic cleavage of a polypeptide, or using recombinant DNA technology.

As to the antibodies that can be elicited by the epitopes of the polypeptides of the invention, whether the epitopes have been isolated or remain part of the polypeptides, both polyclonal and monoclonal antibodies may be prepared by conventional techniques. See, for example, *Monoclonal Antibodies, Hybridomas: A New Dimension in Biological Analyses,* Kennet et al. (eds.), Plenum Press, New York (1980); and *Antibodies: A Laboratory Manual,* Harlow and Land (eds.), Cold Spring Harbor Laboratory Press, Cold Spring Harbor, N.Y., (1988).

Hybridoma cell lines that produce monoclonal antibodies specific for the polypeptides of the invention are also contemplated herein. Such hybridomas may be produced and identified by conventional techniques. One method for producing such a hybridoma cell line comprises immunizing an animal with a polypeptide; harvesting spleen cells from the immunized animal; fusing said spleen cells to a myeloma cell line, thereby generating hybridoma cells; and identifying a hybridoma cell line that produces a monoclonal antibody that binds the polypeptide. The monoclonal antibodies may be recovered by conventional techniques.

The monoclonal antibodies of the present invention include chimeric antibodies, e.g., humanized versions of murine monoclonal antibodies. Such humanized antibodies may be prepared by known techniques and offer the advantage of reduced immunogenicity when the antibodies are administered to humans. In one embodiment, a humanized monoclonal antibody comprises the variable region of a murine antibody (or just the antigen binding site thereof) and a constant region derived from a human antibody. Alternatively, a humanized antibody fragment may comprise the antigen binding site of a murine monoclonal antibody and a variable region fragment (lacking the antigen-binding site) derived from a human antibody. Procedures for the production of chimeric and further engineered monoclonal antibodies include those described in Riechmann et al. (*Nature* 332: 323, 1988), Liu et al. (*PNAS* 84:3439, 1987), Larrick et al. (*Bio/Technology* 7:934, 1989), and Winter and Harris (*TIPS* 14:139, May, 1993). Procedures to generate antibodies transgenically can be found in GB 2,272,440, U.S. Pat. Nos. 5,569,825 and 5,545,806 and related patents claiming priority therefrom, all of which are incorporated by reference herein.

Antigen-binding fragments of the antibodies, which may be produced by conventional techniques, are also encompassed by the present invention. Examples of such fragments include, but are not limited to, Fab and F(ab')$_2$ fragments. Antibody fragments and derivatives produced by genetic engineering techniques are also provided.

In one embodiment, the antibodies are specific for the polypeptides of the present invention and do not cross-react with other proteins. Screening procedures by which such antibodies may be identified are well known, and may involve immunoaffinity chromatography, for example.

Uses Thereof

The antibodies of the invention can be used in assays to detect the presence of the polypeptides or fragments of the invention, either in vitro or in vivo. The antibodies also may be employed in purifying polypeptides or fragments of the invention by immunoaffinity chromatography.

Those antibodies that additionally can block binding of the polypeptides of the invention to RGL ligands may be used to inhibit a biological activity that results from such binding. Such blocking antibodies may be identified using any suitable assay procedure, such as by testing antibodies for the ability to inhibit binding of RGL peptides to certain cells expressing the binding partner(s). Alternatively, blocking antibodies may be identified in assays for the ability to inhibit a biological effect, such as the induction of apoptosis, the interaction of RGL with certain cell types.

Such an antibody may be employed in an in vitro procedure, or administered in vivo to inhibit a biological activity mediated by the entity that generated the antibody. Biological activities caused or exacerbated (directly or indirectly) by the interaction of RGL peptides with cell thus may be modulated. A therapeutic method involves in vivo administration of a blocking antibody to a mammal in an amount effective in inhibiting the targeted biological activity. Monoclonal antibodies are generally preferred for use in such therapeutic methods. In one embodiment, an antigen-binding antibody fragment is employed.

Antibodies may be screened for agonistic (i.e., ligand-mimicking) properties. Such antibodies, induce biological effects (e.g., transduction of biological signals) similar to the effects initiated by interactions between the RGL peptide and given cell. Agonistic antibodies may be used to induce apoptosis or anti-neoplastic biological activities.

Compositions comprising an antibody with specificity for either an RGL peptide or an RGL ligand, and a physiologically acceptable diluent, excipient, or carrier, are provided herein.

Also provided herein are conjugates comprising a detectable (e.g., diagnostic) or therapeutic agent, attached to the antibody. Examples of such agents are presented above. The conjugates find use in in vitro or in vivo procedures.

EXAMPLES

The following examples are provided to further illustrate particular embodiments of the invention, and are not to be construed as limiting the scope of the present invention.

Example 1

Isolation and Identification of the RGL Nucleic Acid

A cDNA was identified using homology search and PCR-based approaches that corresponded to a reported sequence; accession MGC26856, RTVP-1/GliPR-Like (RGL) in the NCBI database. RT-PCR analysis indicated that this sequence as well as an unknown cDNA that is identical to RGL except for a 27-base pair/9 amino acid insertion.

Example 2

Identification of RGL as a p53 Target Gene

The DNA sequences of the RGL gene contains various putative consensus p53 binding sites. The RGL sequence corresponds to a genomic sequence reported in the NCBI database, accession AC121761, *Homo sapiens* 12 BAC RP11-585P4. FIG. 3 shows various potential p53 binding sites with the % identity to a p53 consensus sequence displayed in parentheses. Analysis of these sites for p53 binding was performed by functionally linking each such site to a minimal promoter construct. FIG. 4 shows the relative activities of these synthetic p53 binding sites under the control of such a minimal promoter construct (luciferase normalized to β-gal levels using cotransfection of 148-1 PA mouse prostate cancer cells).

Example 3

RGL Mediated Induction of Apoptosis in TSUPr1 Cells

Figure 5:
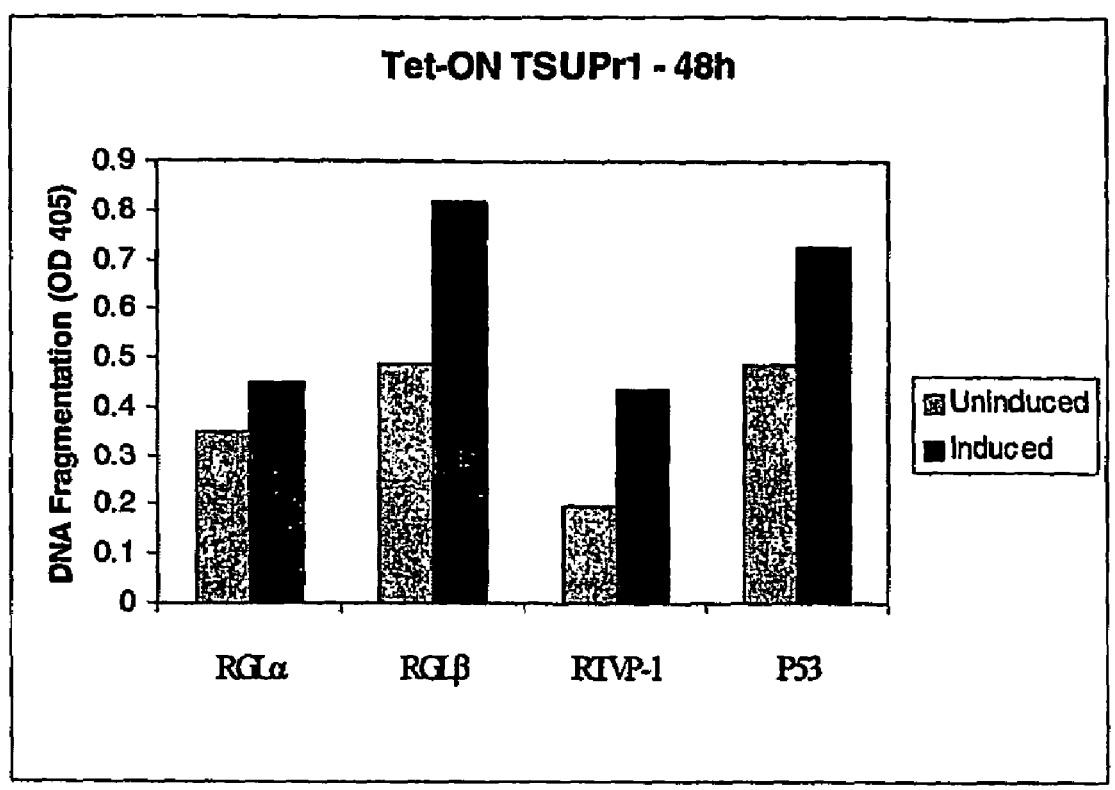
FIG. 5 demonstrates the induction of DNA fragmentation related to apoptosis by expression the amino acid sequences of RGL-alpha and RGL-beta in comparison to that of RTVP-1 in the TSUPr1 cell line.

Apoptosis related DNA fragmentation was analyzed following transfection of TRE-cDNA constructs into stably transfected CMV-rtTA TSUPr1 human prostate cancer cells and stimulation with doxacycline. FIG. 5 demonstrates the ability of RGL-alpha, RGL-beta, RTVP-1 and p53 to induce apoptosis in this cell line.

Example 4

RGL Mediated Suppression of Cell Growth in TSUPr1 Cells

Figure 6:
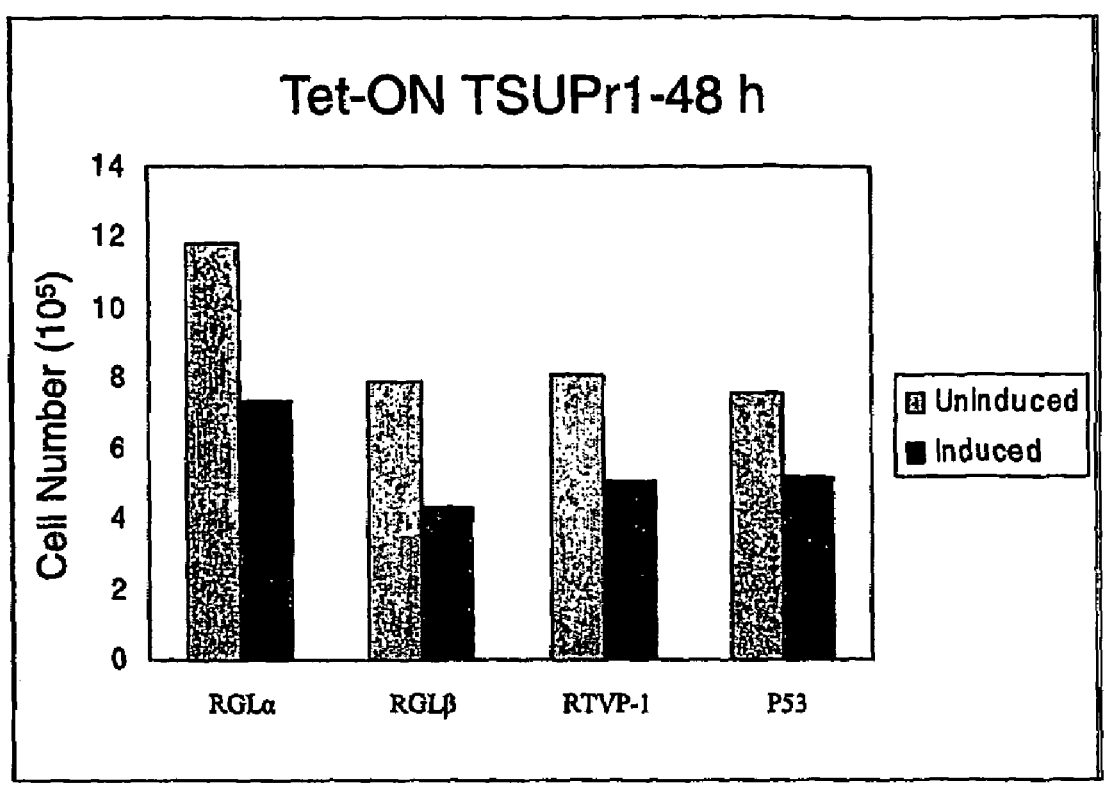
FIG. 6 demonstrates the suppression of cell growth in the TSUPr1 cell line by inducing the expression the amino acid sequences of RGL-alpha and RGL-beta in comparison to that of RTVP-1.

The effect of RGL-alpha, RGL-beta, RTVP-1 and p53 on cell proliferation following transfection of TRE-cDNA constructs into stably transfected CMV rtTA TSUPr1 human prostate cancer cells and stimulation with doxacycline is shown in FIG. 6. The induction of RGL-alpha, RGL-beta, RTVP-1 and p53 expression decreased cell proliferation in this human prostate cancer cell line as measured by direct cell counting.

What is claimed is:

1. An isolated polypeptide encoded by an isolated nucleic acid molecule selected from the group consisting of:
   (a) the DNA sequence of SEQ ID NO:3;
   (b) an isolated nucleic acid molecule encoding an amino acid sequence comprising the sequence of SEQ ID NO:4; or
   (c) an isolated nucleic acid molecule degenerate from SEQ ID NO:3 as a result of the genetic code.

2. The polypeptide of claim 1 in a composition comprising a pharmaceutically acceptable carrier selected from the group consisting of water, oils, alcohols, salts, fatty acids, saccharides, polysaccharides and combinations thereof.

3. The polypeptide of claim 1 wherein the polypeptide has an anti-neoplastic activity.

4. A method for treating a patient comprising administering to the patient a therapeutically effective amount of a composition comprising the polypeptide of SEQ ID NO:4.

5. The method of claim 4 wherein the polypeptide has anti-neoplastic activity.

6. The method of claim 5 wherein the anti-neoplastic activity is a modulation of chemokine expression.

7. The method of claim 5 wherein the anti-neoplastic activity is a modulation of cytokine expression.

8. The method of claim 4 wherein the therapeutically effective amount of the composition is administered locally to a tumor site, systemically, or parenterally.

* * * * *

UNITED STATES PATENT AND TRADEMARK OFFICE
CERTIFICATE OF CORRECTION

| | | |
|---|---|---|
| PATENT NO. | : 7,601,806 B2 | Page 1 of 1 |
| APPLICATION NO. | : 10/559994 | |
| DATED | : October 13, 2009 | |
| INVENTOR(S) | : Thompson et al. | |

It is certified that error appears in the above-identified patent and that said Letters Patent is hereby corrected as shown below:

On the Title page,

[*] Notice:   Subject to any disclaimer, the term of this patent is extended or adjusted under 35 U.S.C. 154(b) by 216 days.

Delete the phrase "by 216 days" and insert -- by 295 days --

Signed and Sealed this

Eighteenth Day of May, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,601,806 B2 | Page 1 of 1 |
| APPLICATION NO. | : 10/559994 | |
| DATED | : October 13, 2009 | |
| INVENTOR(S) | : Timothy C. Thompson, Chenghui Ren and Chengzhen Ren | |

It is certified that error appears in the above-identified patent and that said Letters Patent is hereby corrected as shown below:

On the front page of the patent, after "US 2006/0240025 A1   Oct. 26, 2006", please insert Item (60):

--Related U.S. Application Data
(60)   Provisional application No. 60/477,130, filed on June 9, 2003--

Signed and Sealed this

First Day of June, 2010

David J. Kappos
*Director of the United States Patent and Trademark Office*